United States Patent [19]

Smith et al.

[11] Patent Number: 5,170,800
[45] Date of Patent: Dec. 15, 1992

[54] HERMAPHRODITIC ENDOSCOPIC CLAW EXTRACTORS

[75] Inventors: Kevin W. Smith, Miami; Charles R. Slater, Fort Lauderdale; Thomas O. Bales, Miami; Michael Bacon, Miami, all of Fla.

[73] Assignee: Symbiosis Corporation, Miami, Fla.

[21] Appl. No.: 815,328

[22] Filed: Dec. 27, 1991

Related U.S. Application Data

[63] Continuation-in-part of Ser. No. 680,392, Apr. 4, 1991, and a continuation-in-part of Ser. No. 780,014, Oct. 21, 1991.

[51] Int. Cl.⁵ .............................................. A61B 17/00
[52] U.S. Cl. .................................... 128/751; 606/205; 606/174; 606/170
[58] Field of Search ................ 128/749, 751; 606/167, 606/170, 174, 205, 206, 207, 208

[56] References Cited

U.S. PATENT DOCUMENTS

| | | | |
|---|---|---|---|
| 1,644,581 | 10/1927 | Guyer | 403/97 |
| 2,618,268 | 11/1952 | English | 606/207 |
| 4,688,817 | 8/1987 | Norier | 403/97 |
| 4,760,848 | 8/1988 | Hasson | 606/206 |
| 4,872,456 | 10/1989 | Hasson | 606/207 |
| 4,896,678 | 1/1990 | Ogawa | 128/751 |
| 4,945,970 | 8/1990 | Clossich | 606/205 |
| 4,971,067 | 11/1990 | Boldup et al. | 128/751 |

FOREIGN PATENT DOCUMENTS 0065054  11/1982  France .................. 606/205

Primary Examiner—Kyle L. Howell
Assistant Examiner—Scott R. Akers
Attorney, Agent, or Firm—David P. Gordon

[57] ABSTRACT

End effectors for an endoscopic surgical instrument are provided and comprise a pair of identical elongate longitudinally extending arms having tooth-like terminal projections which closely mesh in a closed position. A preferred embodiment of the end effectors are hermaphroditic claw extractors which grasp and pierce tissue without endangering nearby tissue.

20 Claims, 11 Drawing Sheets

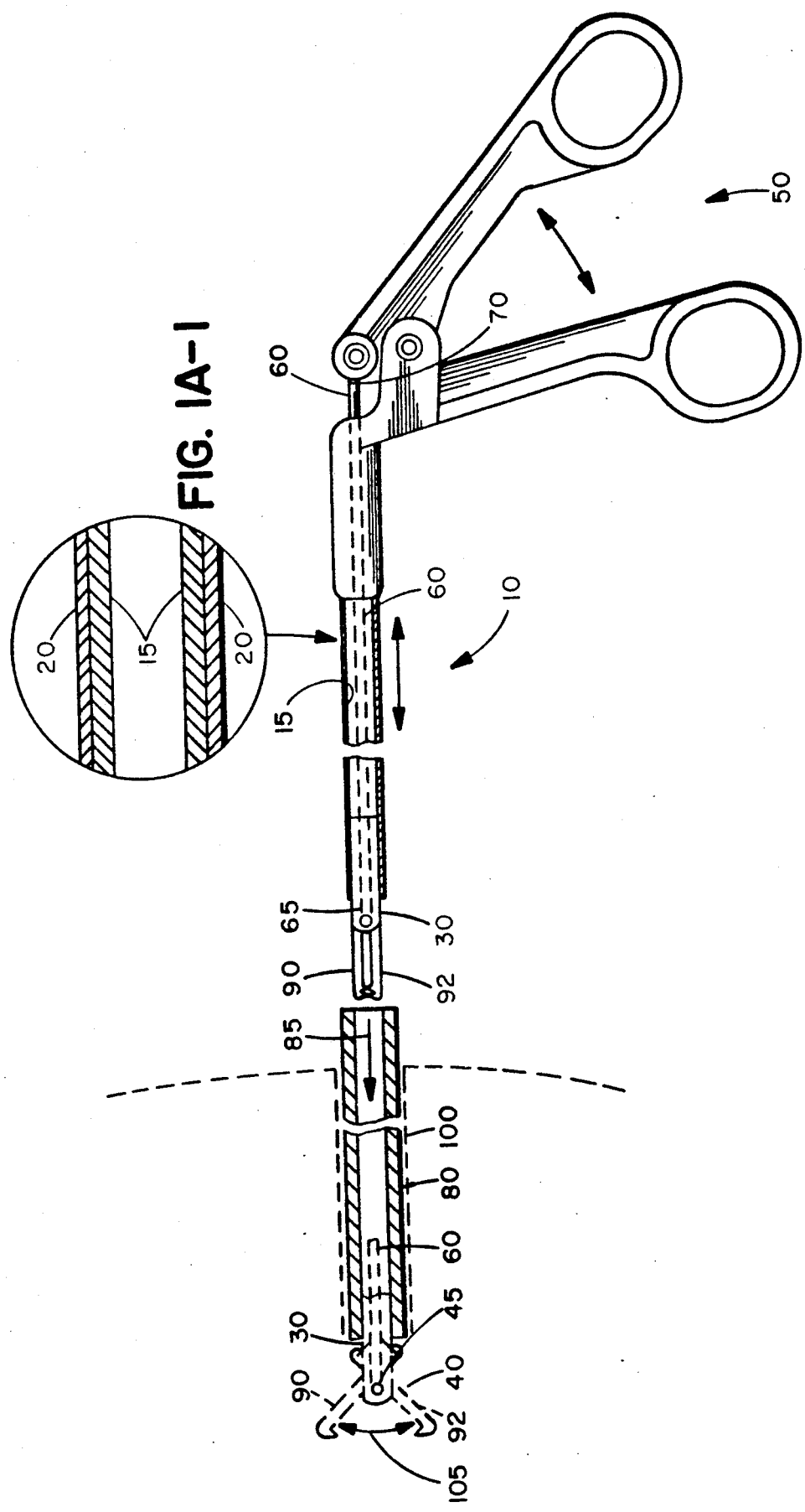

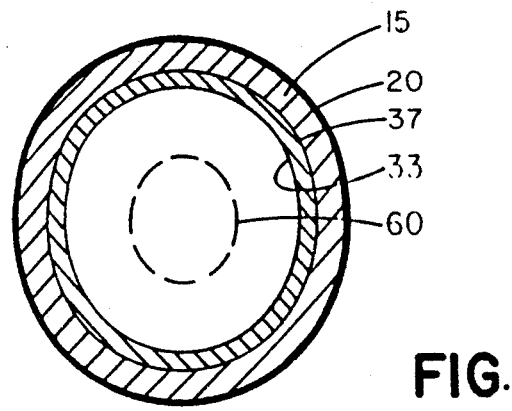
FIG. 2B
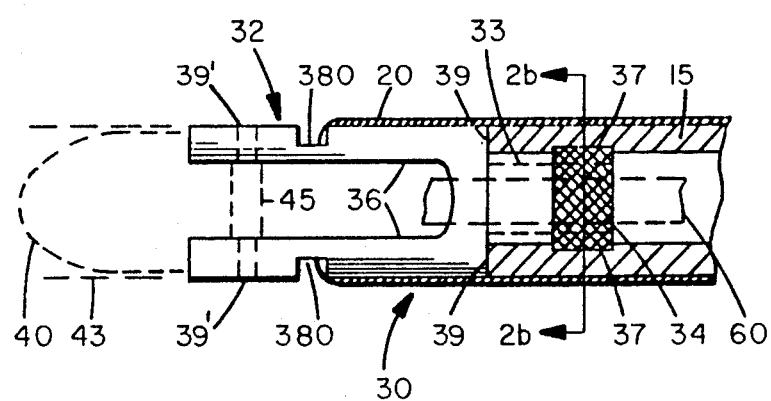
FIG. 2A
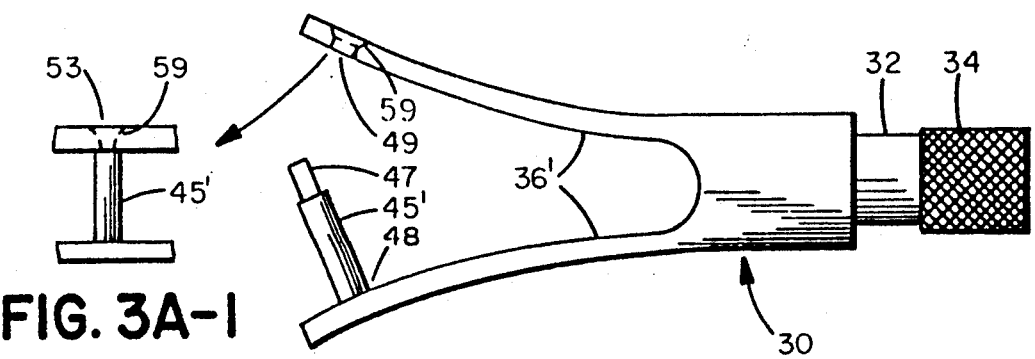
FIG. 3A-1
FIG. 3A

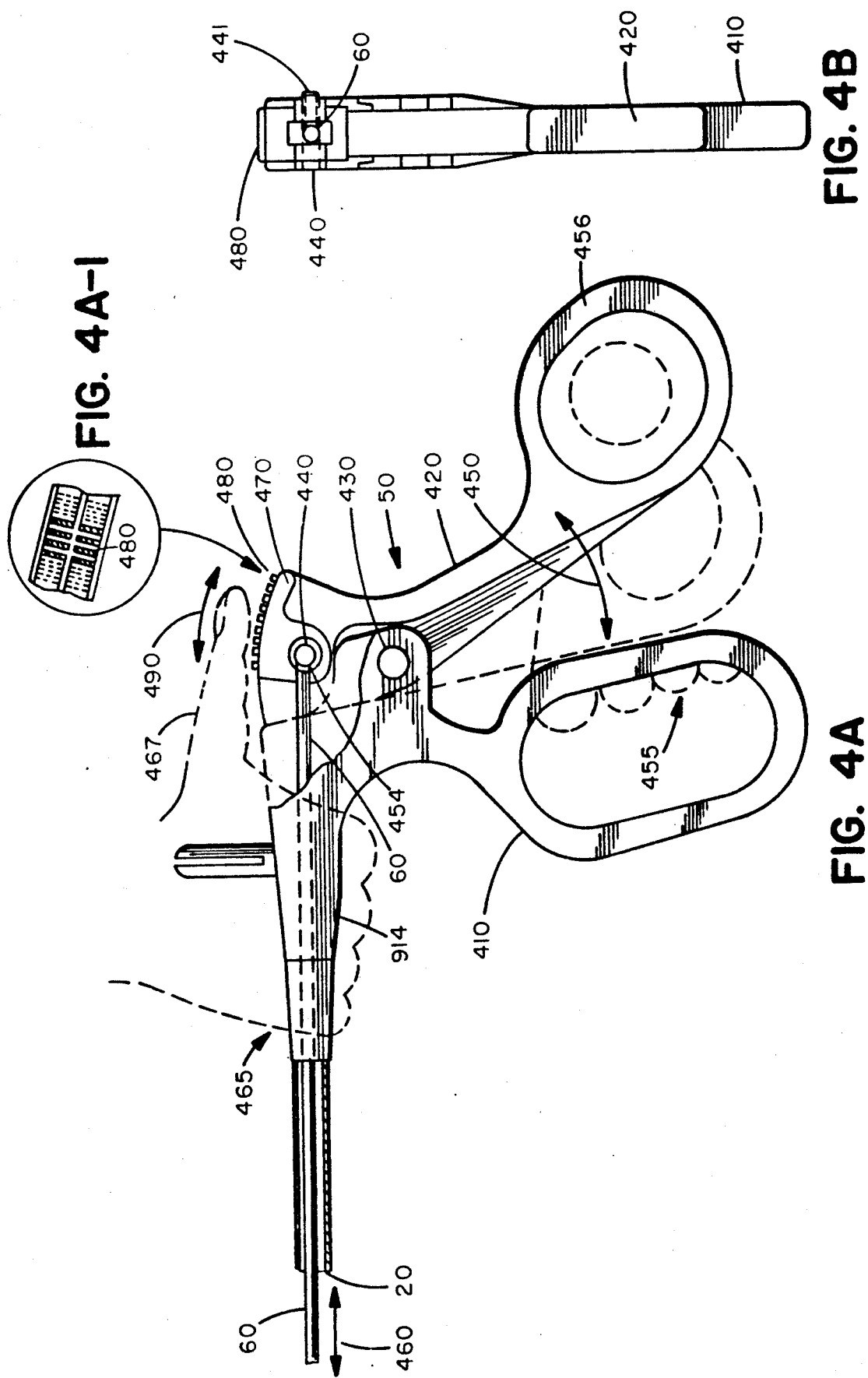

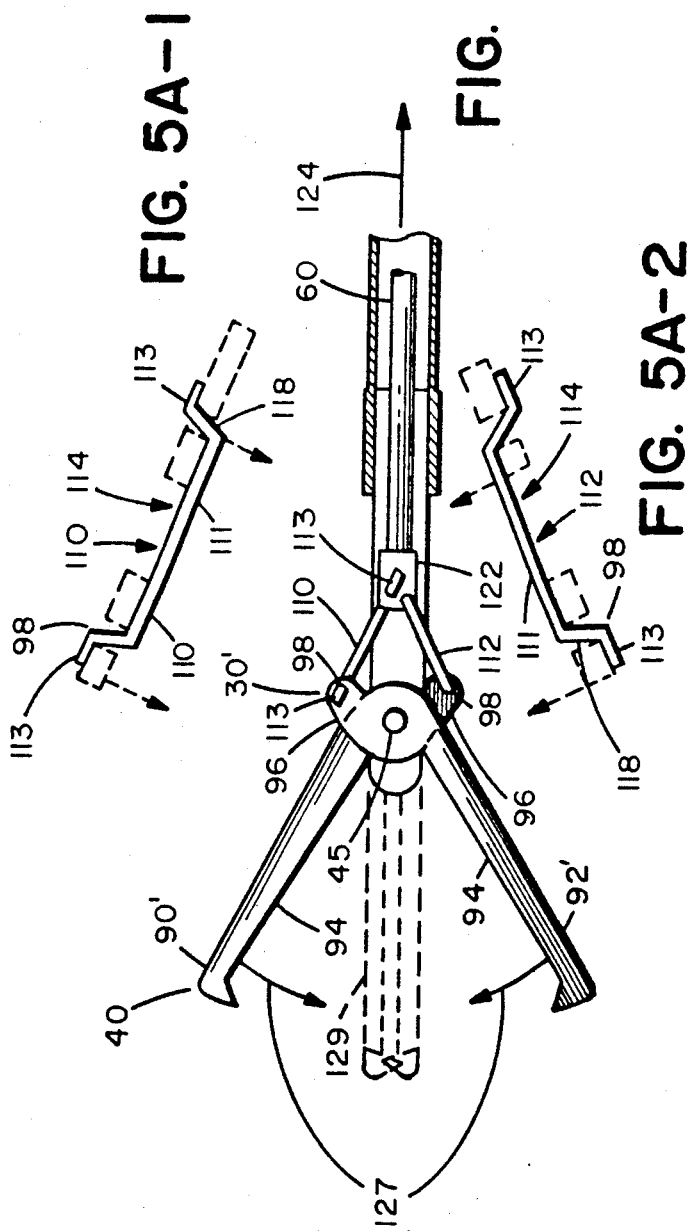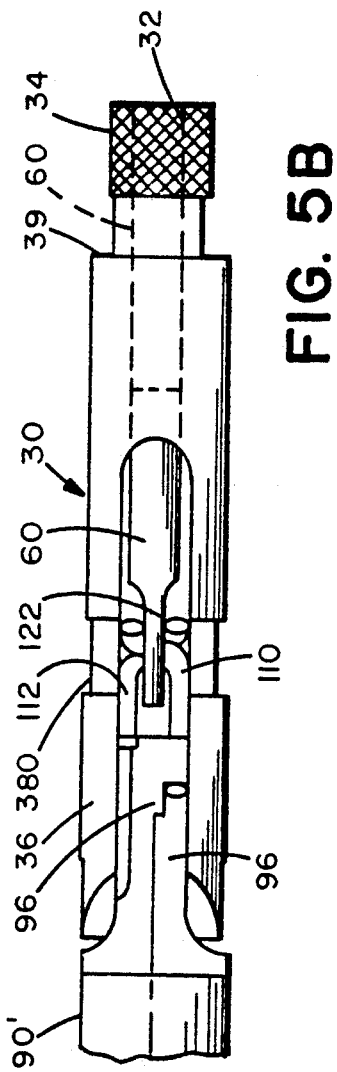

OPEN BLADE POSITION

CLOSED BLADE POSITION

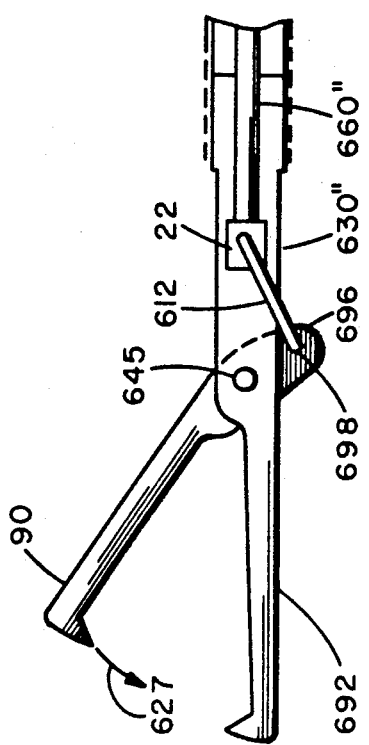
FIG. 6A
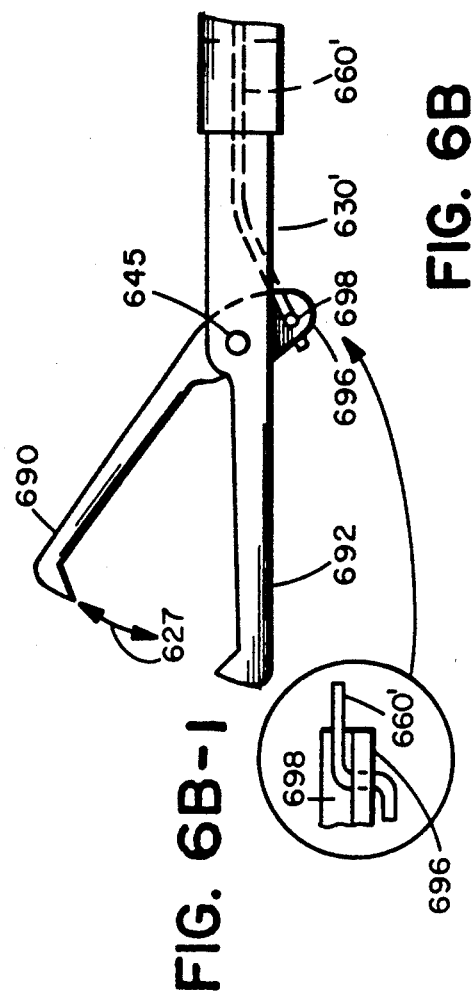
FIG. 6B
FIG. 6B-1
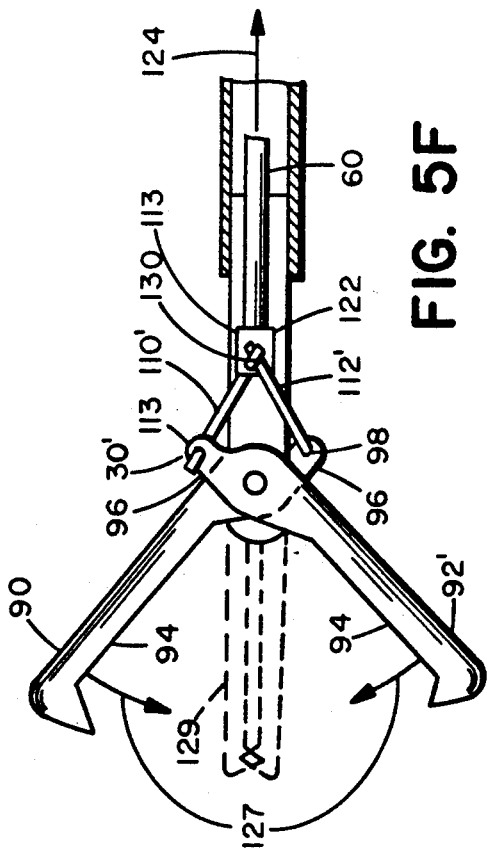
FIG. 5F
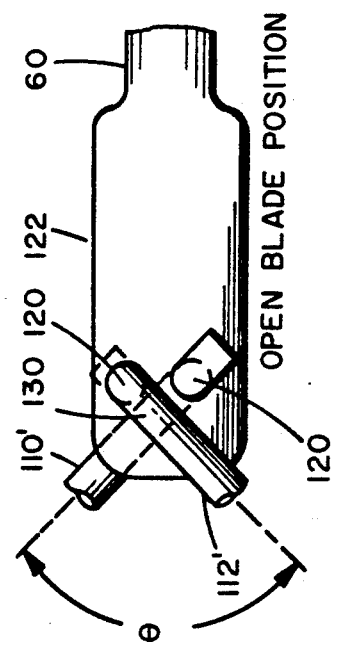
FIG. 5G

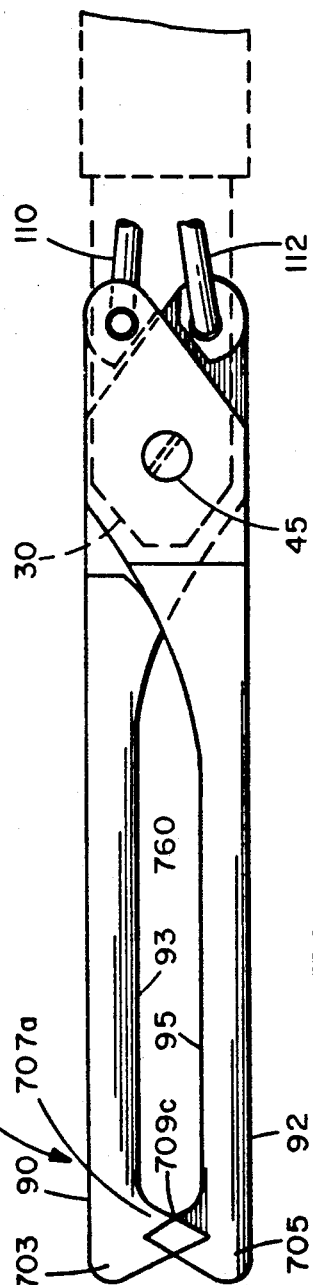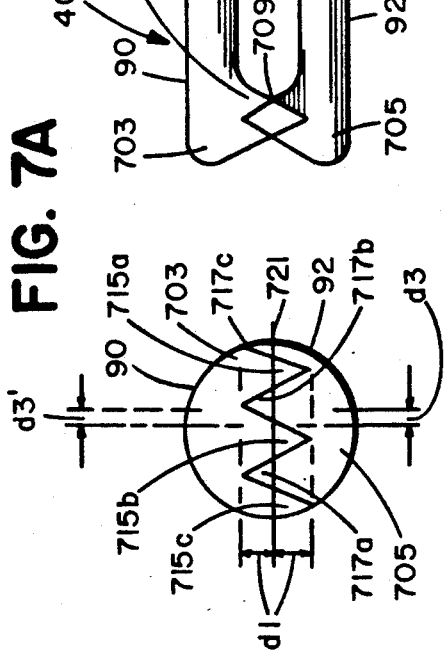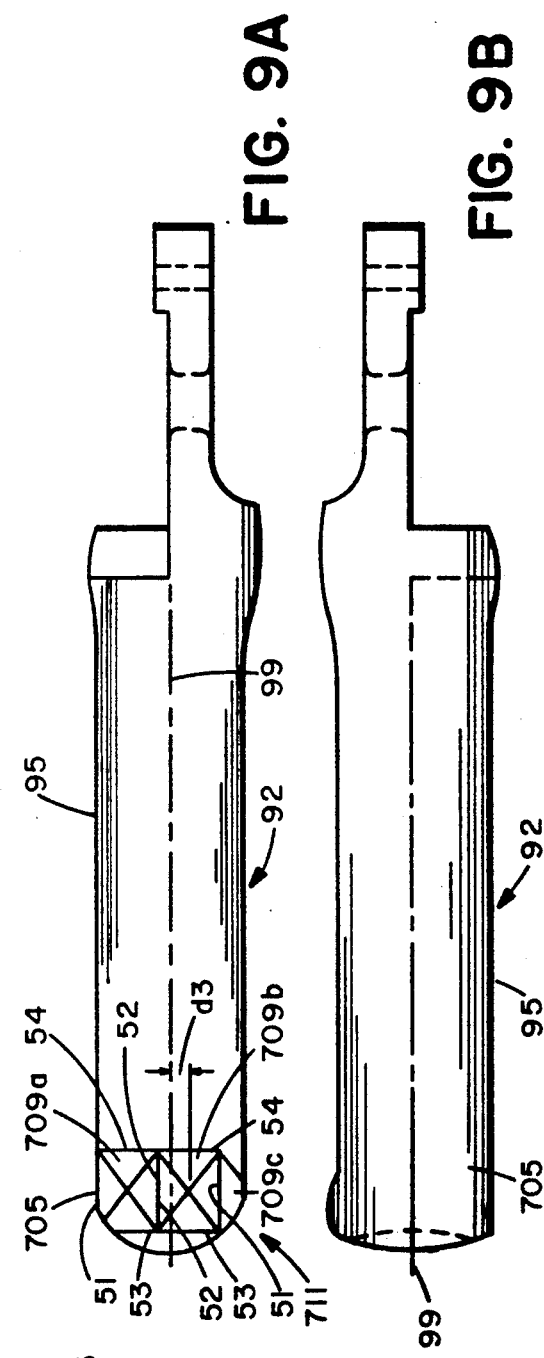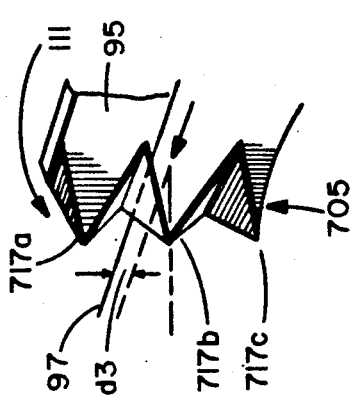

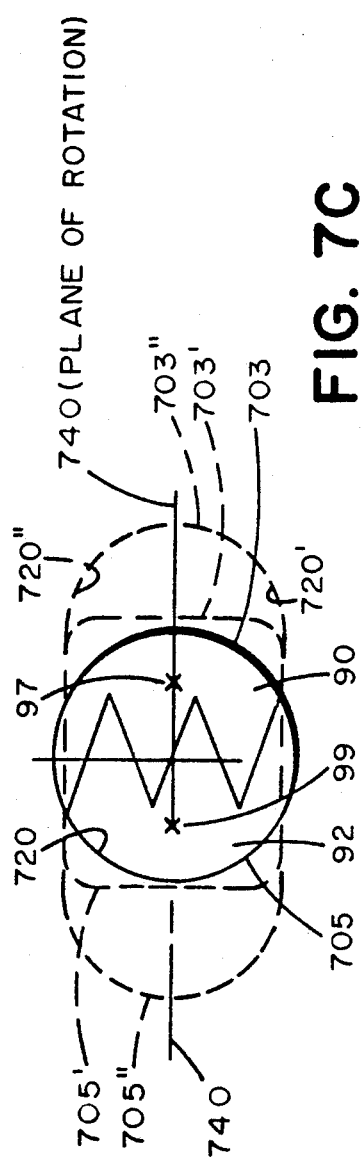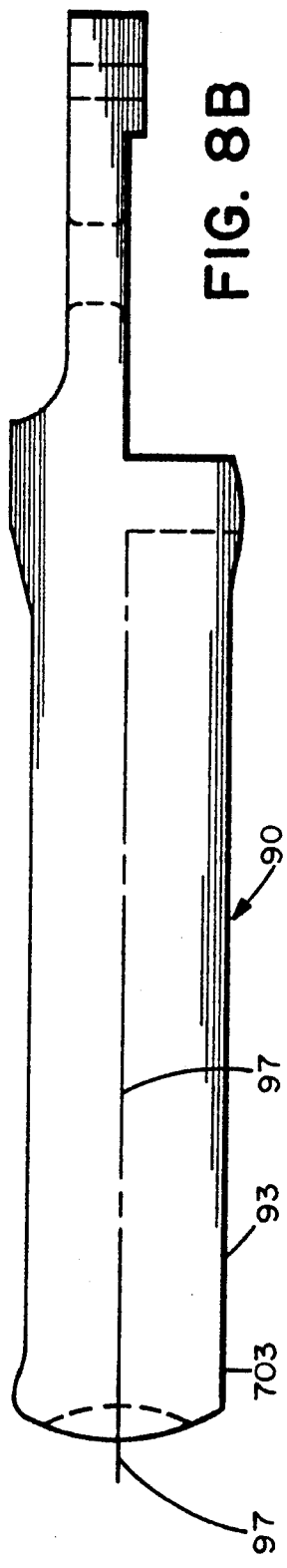

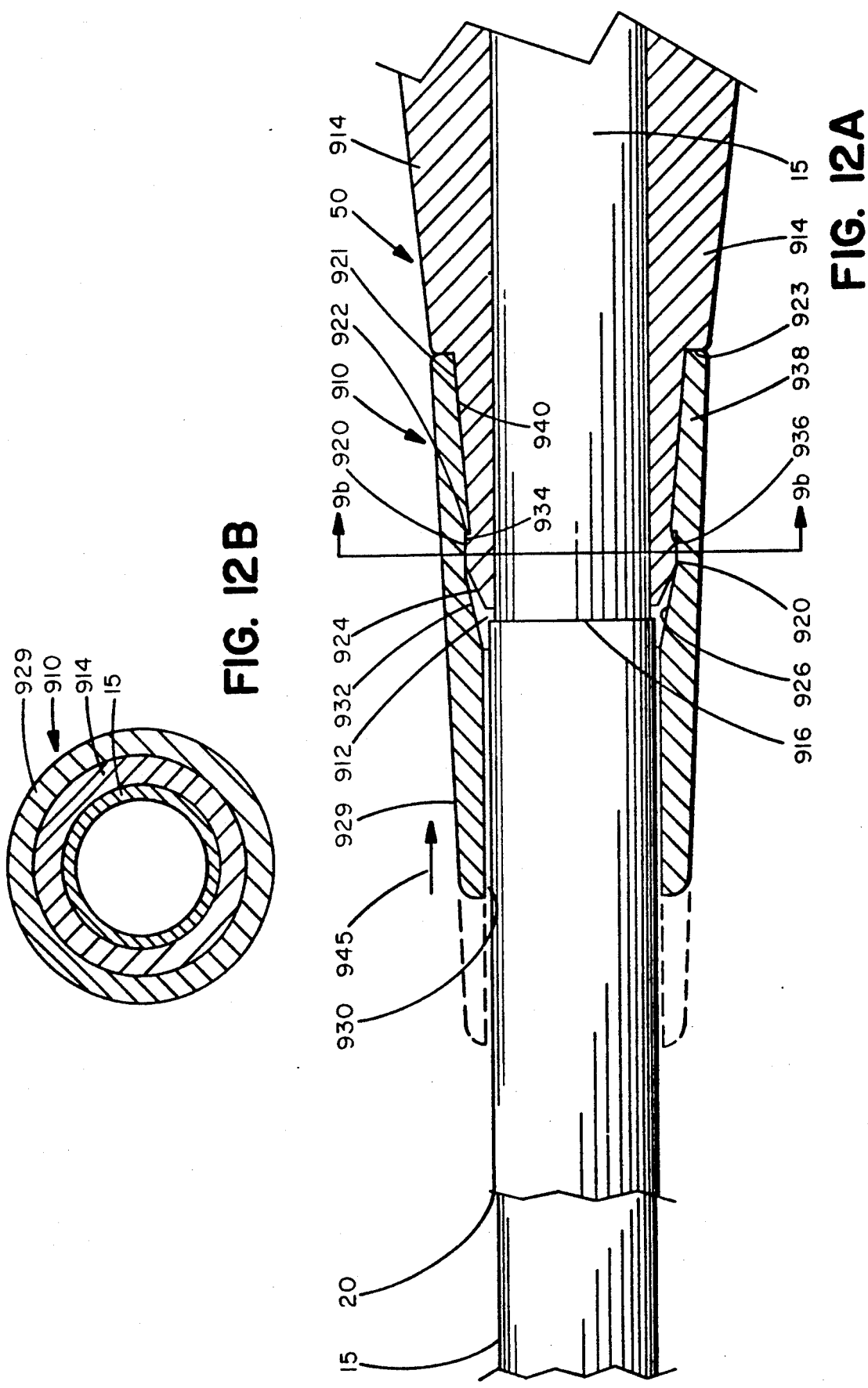

HERMAPHRODITIC ENDOSCOPIC CLAW EXTRACTORS

This is a continuation-in-part of U.S. Ser. Nos. 07/680,392 and 07/780,014 which are hereby incorporated by reference herein in their entireties.

BACKGROUND OF THE INVENTION

The present invention broadly relates to claw extractor surgical instruments. More particularly, the invention relates to disposable endoscopic surgical claw extractors.

The endoscopy and laparoscopy procedures have recently become widely practiced surgical procedures. The endoscopy and laparoscopy procedures involve incising through body walls (e.g., such as the abdominal wall) for examining, viewing and/or operating on the ovaries, uterus, gall bladder, bowels, appendix, etc. Typically, trocars are utilized for creating the incisions. Trocar tubes are left in place in the abdominal wall so that the endoscopic or laparoscopic surgical tools may be inserted through the tube. A camera or magnifying lens is often inserted through a relatively large diameter trocar tube (e.g. 10 mm diameter) which for the laparoscopy procedure is generally located at the navel incision, while a cutter, dissector, extractor, or other surgical instrument is inserted through a typically smaller diameter trocar tube (e.g. 5 mm diameter) for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut or stitched with another surgical instrument; all under view of the surgeon via the camera in place in the navel trocar tube.

The endoscopic and laparoscopic tools of the prior art are primarily reusable stainless steel tools. Between each use of a stainless steel tool, the tool must be soaked, scrubbed, and disinfected. The usual procedure is then to dry the tool, wrap it, and put it in a steam autoclave. The tool is kept sterile until just prior to use when it is removed from the autoclave and unwrapped in the locale of the sterile field of use.

While reusable endoscopic and laparoscopic tools have functioned well for their intended purpose, the process of sterilizing the tool is problematic. Small pieces of tissue or organ often become lodged in the end effectors, and much labor is required to ensure that complete sterility is obtained and maintained. In addition, over time, sharp instruments such as a scissors get dull and must be discarded. However, prior to use of a particular instrument, the surgeon is not able to discern the state of the instrument and whether the instrument will satisfy the surgeon's requirements.

The alternative to reusable endoscopic and laparoscopic surgical tools are disposable tools. However, the complicated construction of endoscopic and laparoscopic surgical tools has typically dictated that the tools be expensive.

SUMMARY OF THE INVENTION

It is therefore an object of the invention to provide well designed disposable endoscopic and laparoscopic surgical instruments where the design reduces the construction cost.

It is another object of the invention to provide disposable endoscopic and laparoscopic surgical instruments having hermaphroditic investment cast end effectors.

It is yet another object of the invention to provide hermaphroditic investment cast claw extractor end effectors for a disposable surgical instrument.

In accord with the objects of the invention, a disposable endoscopic/laparoscopic surgical instrument generally includes: a tube; a push rod which extends through the tube; an actuating means engaging the tube and the push rod for imparting reciprocal axial motion to the push rod; hermaphroditic end effector means coupled to the push rod by linkage means which are also coupled to the push rod; and a clevis coupled to the tube at its proximal end and to the end effector means at its distal end, wherein axial movement of the push rod effects movement of the hermaphroditic end effector means in a plane parallel to the longitudinal axis of the push rod. Plastic shrink wrap is preferably utilized to electrically insulate the disposable instrument and extends over the aluminum tube and over at least an adjacent portion of the clevis. The tube and push rod are preferably made of aluminum, the clevis is preferably made of a high-strength aluminum alloy, the actuating means is preferably made of plastic and aluminum, and the hermaphroditic end effector means is preferably made of investment cast bronze.

In a preferred embodiment of the invention, the hermaphroditic end effectors are claw extractors which are suited to strongly grasping and separating diseased tissue. The claw extractor end effectors comprise a pair of identical gripping means, preferably investment cast from an alloy of aluminum bronze. The identical gripping means of the claw extractors have an integral elongate longitudinally extending element with a proximal portion rotatably engaging the clevis means, and an integral forward terminal portion in the form of a row of side-by-side tooth-like elements. The tooth-like elements extend perpendicular to the longitudinal axis of the gripping means. The identical gripping means are arranged oppositely on the tool (i.e., one of the gripping means is flipped or rotated by one hundred eighty degrees relative to the other gripping means) so that when the rotatably engaged gripping means are closed in a clamped position, the tooth-like elements of the respective identical gripping members mesh (mate) in a close fitting contact.

The clevis of the invention is preferably a separately formed clevis having a knurled rod-like proximal end for mating with the end of the aluminum tube, and a post-supporting U-shaped distal portion for holding the end effector means. The post in the distal portion is perpendicular to the legs of the U-shaped distal portion and is arranged to extend through hoe(s) in the end effector means. In this manner, the blades or prongs of the end effector means are held by, but can rotate around the post. Each leg of the U-shaped distal portion of the clevis also preferably includes a notch which serves as a terminating location for the shrink-wrap. Another aspect of the clevis relates to the forming of the post integral with one of the legs of the distal portion of the clevis.

According to one aspect of the invention the push rod is flattened on its distal end, and the linkage means which couples the push rod and the end effector is a staple which extends through a hole in the flattened end of the push rod as well as another hole in the proximal end of the end effector. Because the outer tube is positioned at a fixed distance from the rotation hole in the end effector (due to the clevis), when the push rod is moved axially relative to the tube, the end effector cannot move axially. However, because the push rod is also a fixed distance away from another hole in the proximal end of the end effector (due to the staple), movement of the push rod relative to the tube causes rotation of the end effector in a plane. In other words, movement of the push rod relative to the tube causes the hole through the end effector through which the staple extends to rotate along an arc centered at the rotation hole in the end effector through which the post of the clevis extends. Movement in this manner typically effects a cutting, dissecting or grasping action.

The hermaphroditic end effector means of the invention can be double acting or single acting. Single acting end effectors can include one hole in the flattened end of the push rod and one staple for connecting the moving end effector to the push rod. A double acting end effector correspondingly includes two holes in the flattened end of the push rod and two staples; one for each end effector. If desired, a single acting end effector can eliminate the staple by forming one end of the pull wire into a "dog's leg" and by inserting the dog's leg pull rod end into the hole in the proximal end of the end effector.

A better understanding of the disposable hermaphroditic surgical instruments of the invention, and additional advantages and objects of the invention will become apparent to those skilled in the art upon reference to the detailed description and accompanying drawings.

BRIEF DESCRIPTION OF THE DRAWINGS

FIG. 1 is a side elevation view, partly in section, of a disposable surgical instrument prior to insertion into a trocar tube, and, in partial phantom format, after insertion into a trocar tube;

FIG. 1a-1 is a cross sectional view through the instrument of FIG. 1 at the indicated location;

FIG. 2a is a side elevation view, partly in section, of a clevis usable with the invention in conjunction with the distal end of the tube and shrink wrap of the invention;

FIG. 2b is a cross-section view of the device of FIG. 2a;

FIG. 3 is a side elevation view of an alternate clevis embodiment of the invention prior to assembly with end effectors;

FIG. 3a-1 is a side elevation view of the alternate clevis of FIG. 3 in a closed position;

FIG. 4a is a partially broken-away side elevation view of the actuating handle of the disposable instrument usable with the invention;

FIG. 4b is a rear elevation view of the device of FIG. 4a;

FIG. 4a-1 is a partial top view of the actuating handle of FIG. 4a at the indicated location thereof;

FIG. 5a is a side elevation view, partly in section, of a double acting hermaphroditic claw extractor in conjunction with the clevis and the distal ends of the rod and tube of the disposable instrument usable with the invention;

FIGS. 5a-1 and 5a-2 show perspective views of the staple linkage means of FIG. 5a;

FIG. 5b is a plan view of the device of FIG. 5a;

FIG. 5c is an enlarged side view of the connection of the distal end of the rod and the proximal ends of the staple linkage means of FIG. 5a;

FIG. 5f is a side elevation view of a double acting claw extractor utilizing a crossed staple linkage means;

FIG. 5g is an enlarged top view of the distal end of the rod and the proximal end of the crossed staple linkage means;

FIG. 6a is a side elevation view of a first embodiment of a single acting claw extractor of the invention in conjunction with the clevis, and the distal ends of the rod and tube of the disposable instrument;

FIG. 6b is a side elevation view of a second embodiment of a single acting claw extractor;

FIG. 6b-1 shows a perspective view of the push-rod, end effector connection of the single acting scissors of FIG. 6b;

FIG. 7 is a side elevation view of the claw extractor end effectors of the present invention in a closed position;

FIG. 7a is a front elevation view of the device of FIG. 7;

FIG. 7c shows variations in the periphery of the forward projection of FIG. 7a;

FIGS. 8a, 8b are top and bottom plan views of the upper end effector claw extractor element of the device shown in FIG. 7;

FIGS. 9a, 9b are top and bottom plan views of the lower end effector claw extractor element of the device shown in FIG. 7;

FIG. 9A-1 shows a partial perspective view of the teeth of FIG. 9a;

FIG. 12a is a side elevation view in section of a ferrule shielding device of the present invention engaged with the shrink wrapped aluminum tube and handle of the invention; and FIG. 12b is a cross-section view of the device of FIG. 12a.

DETAILED DESCRIPTION OF THE PREFERRED EMBODIMENT

Figure 10A:
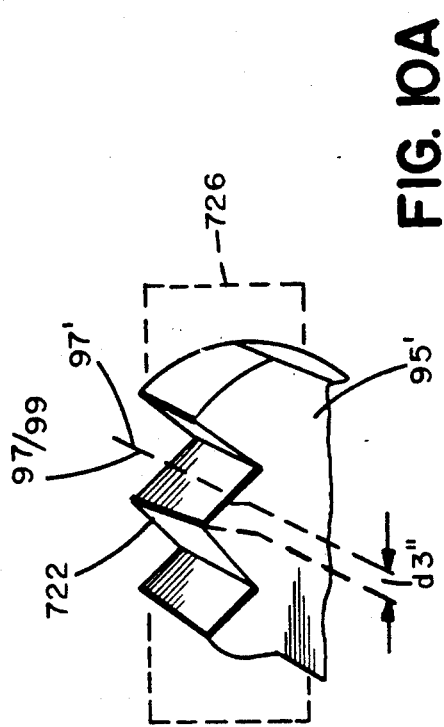
FIGS. 10a, 10b show alternate forms of tooth-like elements for the device of FIG. 7.

With reference to FIGS. 1 and 1a-1, a disposable endoscopic or laparoscopic surgical instrument is indicated at 10. The disposable surgical instrument 10 broadly comprises an aluminum tube 15 surrounded by a peripheral insulating shrink wrap layer of plastic 20, a clevis means 30, end effectors 40, actuating means 50, and a push rod 60. The clevis means 30 is advantageously a separately formed aluminum piece which fixedly engages aluminum tube 15 as described in more detail hereinafter. The clevis 30 also engages the end effectors 40 which are pivotally engaged to clevis 30 at pivot pin 45. The end effectors 40 are preferably formed of investment cast bronze as disclosed in copending U.S. Ser. No. 07/521,766 which is hereby incorporated by reference herein. The push rod 60, which is also formed of aluminum, is engaged at its distal end 65 to the end effectors 40, as hereinafter more fully described, and is connected at 70, at its proximal end to a manually operable actuating means 50. For purposes herein, the "distal end" of the instrument 10 or any part thereof, is the end closest to the surgical site and distant from the surgeon, while the "proximal end" of the instrument 10 or any part thereof, is the end most proximate the surgeon and distant the surgical site.

In use, the instrument 10 is inserted with the graspers 90, 92 of the end effector 40 in the closed position, into trocar tube 80, as indicated at the arrow 85 of FIG. 1. The distal portion of the instrument 10 passes through the trocar tube 80 into body incision 100. Upon the distal portion of the laparoscopy instrument 10 exiting the trocar tube 80, the graspers 90, 92 can be opened and closed as indicated at 105 by reciprocal motion of push rod 60 which results from operation of the manual actuating means 50. As is discussed more fully hereinafter, the clevis effectively translates the reciprocal motion of the push rod 60 into the end effector means action indicated at 105.

Turning to FIGS. 2a and 2b, a preferred configuration of the clevis 30 of the present invention is seen. The clevis has a knurled rod-like proximal portion 34 for mating with the end of the aluminum tube 15, and a post-supporting U-shaped distal portion 32 for holding the end effector means. The outer diameter of the distal portion 32 of the clevis is larger than the outer diameter of the proximal portion 34; shoulder 39 being formed therebetween. The proximal portion 34 of the clevis is preferably hollow, as indicated at 33, to permit the push rod 60 to extend therethrough. The distal portion 32 of the clevis 30 is provided with legs 36 and a post or pivot pin 45. The post 45 is generally perpendicular, i.e. transverse, to the legs 36 of the clevis and is arranged to extend through hole(s) 39 in the end effector means 40. In this manner, the blades or prongs of the end effector means 40 are held by, but can rotate around, i.e. are rotatably engaged with the post 45.

As seen in FIG. 2a, a recess or notch 380 is provided which extends across each leg 36 of the clevis 30. Consequently, a peripherally applied electrically insulating plastic wrap 20 can be end-cut at recess 380 and a smooth transition from the end effector means 40 via the clevis 30 to tube 15 can be achieved. Even if slight outward flaring of wrap 20 occurs at the end-cut, as is common, this flaring can be tolerated as it will be within the envelope of the normal outer surface indicated at 43, and thus the shrink wrap will not snare on the trocar tube as it is extended therethrough. Another preferred manner of eliminating the possibility of snaring is to maintain the outer diameter across the legs 36 of the clevis 30 at the same width as the outer diameter of the aluminum tube 15, but to increase the diameter of the distal end of the legs slightly, and to end the shrink wrap where the legs increase in width. Thus, the shrink wrap will be "in the shadow" of the wider forward portion and will not snare, even if there is a slight flare.

Clevis 30 is preferably made from a high strength aluminum base alloy (e.g. 2024 alloy of Alcoa) which is preferably harder than the aluminum base alloy (e.g. 6061 or 6063 alloys of Alcoa) from which tube 15 is fabricated. The post portion of the clevis may be made out of the identical alloy or, for added strength, out of a stainless steel nail. In assembly of the laparoscopy surgical instrument 10, serrated or knurled portion 34 of clevis 10 is fit snugly into tube 15 such that the walls of tube 15 abut the peripheral shoulder 39 of clevis 30, with the outer surface of tube 15 and the adjacent outer surface of clevis 30 having essentially the same diameter. Mechanical pressure is then applied to tube 15 peripherally at the location of knurled portion 34, thereby crimping the end portion of tube 15 onto the knurled portion 34. Mechanical pressure causes the projections of the knurls to bite into and firmly engage tube 15 as indicated at 37 due to the higher hardness of the clevis material. Once the clevis 30 and tube 15 have been properly joined, the plastic shrink wrap 20 can be applied over the tube 15 and an adjacent portion of the clevis 30 and end-cut at recess 380.

FIG. 3 shows an alternate embodiment for the clevis means of the present invention wherein the clevis 30 is formed and machined from aluminum base alloy as one integral element. As seen in FIG. 2b, the arms 36' of clevis 30 are bent outwardly away from each other. Pivot pin 45' is integral with one arm 36' as indicated at 48 and has a terminal portion 47 of reduced diameter which will engage slightly larger hole 49 when the arms 36 are bent inwardly and parallel with each other (i.e. after end effectors 40 of FIG. 2a are attached). Upon bending of the arms 36', the tip of terminal portion 47 engages and is suitably flattened in recess 59 as indicated at 53 of FIG. 3a-1.

With reference to FIGS. 4a, 4a-1, and 4b, manually operable actuating means are indicated at 50 which includes an electrically insulating housing 914 having a fixed handle portion 410 integral therewith and a lever portion 420 pivotally engaged to housing 914 at pivot pin 430. Push rod 60 passes through aluminum tube 15 (covered by shrink wrap 20) and engages cross pin 440 at 454; set screw 441 being used to extend into cross pin 440 and set push rod 60 in the cross pin 440. The cross pin 440 is fixedly positioned in lever member 420. Upon pivotal motion of lever arm 420, as indicated at 450, using a conventional hand grip as indicated at 455 to apply pressure to extended handle element 456 of lever member 420, push rod 60 will move linearly as indicated at 460 to actuate an end-effector (not shown in FIG. 4a) coupled thereto as hereinabove described. There may be occasions, in the course of certain laparoscopic procedures, that certain surgeons will prefer to hold the actuating means 50 in the manner indicated at 465 with fingers grasping housing 914 and the thumb 467 adjacent a portion 470 of lever member 420 which is positioned on the opposite side of cross-pin 440 from extended handle element 456. Thus, in accord with one aspect of the invention, a roughened knurled or serrated surface 480 is provided integral with portion 470 of lever member 420 to enable a frictional engagement with thumb 467. Utilizing serrated surface 480, when thumb motion as indicated at 490 is initiated, pivotal motion of lever arm 420 is accomplished, as indicated at 450, as is the linear motion of push rod 60 as indicated at 460.

With reference to FIGS. 5a, 5a-1, 5a-2, and 5b-g, details are seen of an end effector 40 and the linkage means for linking the end effector 40 to the push rod 60. In particular, in FIGS. 5a-5g, a double acting claw extractor is shown with graspers 90', 92' which are respectively rotatably mounted on pivot pin 45 of clevis 30'. Each grasper 90', 92' of the claw extractor has a forwardly extending manipulating portion 94, and a rearwardly extending planar base portion 96 with a through-hole 98. Each of the through-holes 98 of planar base portions 96 is separately engaged by a separate connecting or linkage means 110, 112.

As shown in FIGS. 5, 5a-1 and 5a-2, according to one preferred embodiment, each linkage means 110, 112 is in the form of a thin metal member generally in the shape of an outwardly flared staple. Each linkage means may be generally described as having a U-shaped section 114 with a base 111 perpendicular to and bridging the arms 118 of the U, and two generally parallel spaced apart outwardly extending side or tab elements 113 which are generally parallel to base 111. Each of the linkage means 110, 112 has one of its tab elements 113 engaged in a through-hole 98 of a planar base 96, with the U-shaped section of the linkage means extending respectively in opposite directions as illustrated. The other tab element 113 of the linkage means 110, 112 engage through-holes 120 formed in a flattened plate-like terminal portion 122 of push rod 60 (as seen more clearly in FIGS. 5d-5f). As can be seen from FIG. 5a, movement of push rod 60 in the direction indicated at 124 will cause blades 90', 92' to move in the direction indicated at 127 to the position 129 without interference between the oppositely positioned staple-like linkage means 110, 112. Correspondingly, the tab elements 113 of the linkage means 110, 112 which extend through the flattened terminal portion 122 of push rod 60 will move from their position shown in FIG. 5d, to the position shown in FIG. 5e.

That manipulators or graspers 90' and 92' open and close in response to the axial movement of push rod 60 may be understood by understanding the relationship of the clevis 30' and linkage means 110, 112 to the graspers 90', 92', the push rod 60, and the tube 15. In particular, due to the fact that the clevis 30' is rigidly attached to the tube 15 (as described above with reference to FIG. 2a), the tube 15 is a fixed distance from the rotation pin 45 of the clevis, and hence to the holes in the graspers 90' and 92' through which rotation pin 45 extends. Thus, when the push rod 60 is moved axially relative to the tube 15 (the tube being fixed in place), the graspers of the end effector cannot move axially with the push rod. However, because the push rod 60 is also a fixed distance away from holes 98 in the base portion of the end effector graspers (due to staple linkage means 110, 112), movement of the push rod relative to the tube must cause movement of the holes 98 in the end effector graspers. Because one part each grasper is fixed, but another part must move when the push rod 60 is moved relative to the tube 15, end effector graspers 110 and 112 rotate along an arc centered at the fixed rotation hole in the end effector through which the post 45 of the clevis 30' extends. Movement in this manner typically effects a cutting or grasping action.

FIGS. 5f and 5g show another embodiment of the linkage means which increases the stability of the end effector means 40. In FIGS. 5g and 5h it is seen that the linkage means 110', 112' do not respectively engage the nearest of the through-holes 120 transversely aligned in the plate-like terminal portion 122 of push rod 60, but instead cross-over as indicated at 130. With this arrangement the angle Θ, indicated at 135, is increased. The increase in this angle affords a more stable instrument, because the amount of "shake" which results from the unavoidable clearances at the pivot 45 is reduced; i.e., as Θ approaches 90°, the amount of free movement at the end of an end-effector blade 90', 92' is minimized.

FIG. 6a shows a single acting claw extractor device. Essentially, the single acting device is identical to the double acting device of FIGS. 2a-2g except that blade 692 is stationary; hence no staple is used to connect blade 692 to rod 660. While blade 692 is stationary, blade 690 pivots as indicated at 627 around pin 645. To ensure rotational movement of blade 690 upon axial movement of rod 660, the end 622 of rod 660 should be supported.

FIGS. 6b and 6b-1 show a preferred embodiment of a single acting claw extractor where instead of utilizing a pull rod with a flattened end, pull rod 660' is a very thin wire of staple thickness (e.g. 25 mils) which has a rigid dog's-leg or zigzagged end which extends through hole 698 of the proximal end of the claw extractor end effector 690. A similar pull rod is shown in previously incorporated U.S. Ser. No. 07/521,766, where instead of a single acting claw extractor, a radial jaw biopsy forceps is shown.

Figure 7B:
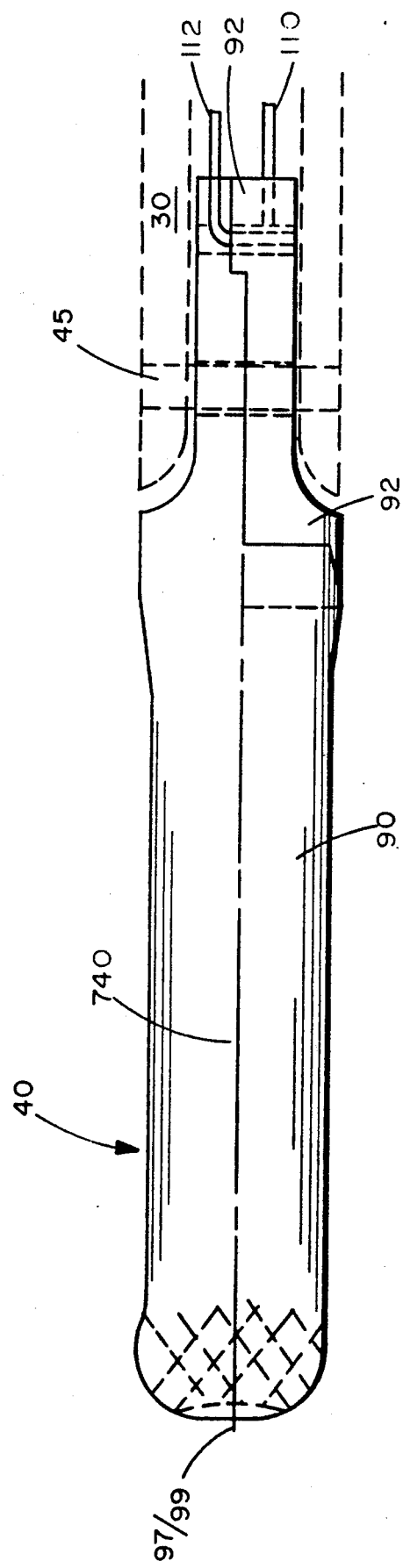
FIG. 7b is a top plan view of the device of FIG. 7.

With reference to FIGS. 7, 7a, 7b the hermaphroditic claw extractor end effectors of the present invention are indicated at 40 and include identical gripping means (claws) 90 and 92 which are shown separately in FIGS. 8a, 8b and 9a, 9b. Because gripping means 90 and 92 are essentially identical they are preferably investment cast from a single mold, thereby reducing the overall cost of the surgical instrument. The preferred claw extractor gripping means 90, 92 each have a longitudinally extending elongate element 93, 95 with respective correspondingly located longitudinal axes 97, 99. Gripping means 90, 92 also each have respective forward (distal) terminal portions 701, 703 having sharp, tooth-like elements 707(a) ... (n) and 709(a) ... (n) project in a plane perpendicular to the longitudinal axes 97, 99. In the preferred embodiment shown in FIGS. 8a, 9a and 9a-1, the projecting tooth-like elements are quadrilaterally based equal sided pyramids. The tooth-like elements 707(a)-(n), 709(a)-(n) are arranged adjacently side-by-side in rows 711, 713 which are perpendicular to the respective longitudinal axes 97, 99 of elongate elements 90, 92. Each row 711, 713 includes at least two tooth-like elements, and preferably includes two substantially fully formed tooth-like elements 707(a)-(b), 709(a)-(b) (teeth 707(a) and 709(a) being slightly rounded on face but still being substantially full) and a partially formed tooth-like element 707(c), 709(c) which would be essentially identical to teeth 707(a)-(b), 709(a)-(b) if fully formed.

Figure 10B:
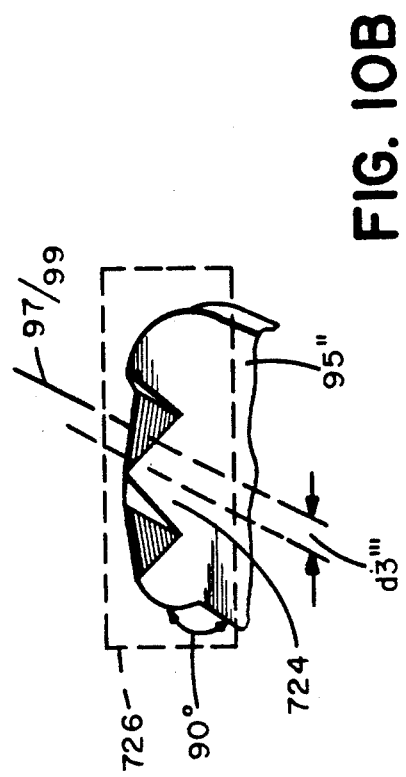
Figure 5C:
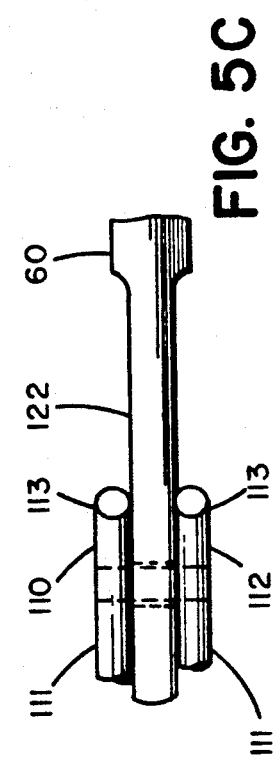
Figure 5D:
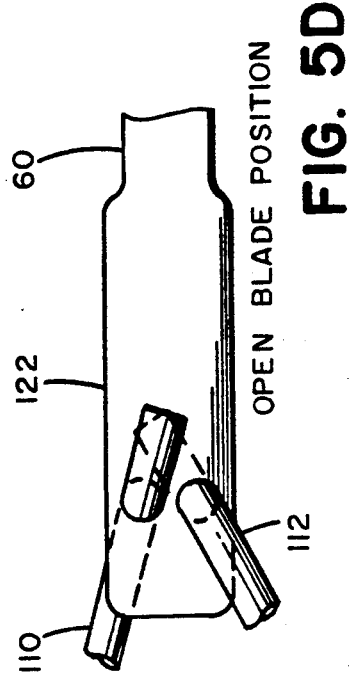
FIGS. 5d and 5e are enlarged top views of the distal end of the rod and the proximal ends of the staple linkage means when the blades of the end effectors are in open and closed positions respectively.
Figure 5E:
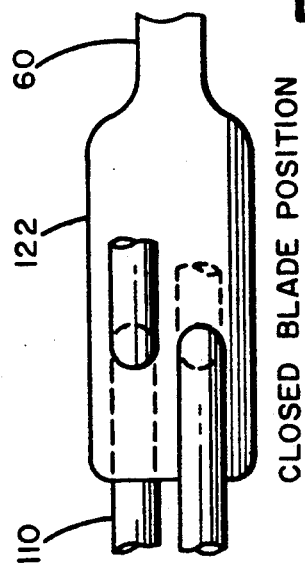

As shown particularly in FIGS. 8(a), 9(a) and 9a-1 the rows 711, 713 of tooth-like elements commence with substantially fully formed quadrilaterally based pyramids 707(a), 709(a) which join contiguous, intermediate substantially fully formed pyramids 707(b), 709(b) and terminate with partially formed pyramids 707(c), 709(c). The fully formed pyramids 707(a)-(b) and 709(a)-(b) each have two equal parallel sides, s1, s2 parallel to longitudinal axes 97, 99 and two equal parallel sides s3, s4 perpendicular to longitudinal axes. The pyramids are all in-line and equally displaced from and at a common level from a plane 721 of longitudinal axes 97/99 as indicated at d1 in FIG. 7(a). The apex 717(b) (and hence apex 717(a)) of intermediate pyramidal tooth-like element 109(b) is displaced from longitudinal axis 99 in a direction transverse to the longitudinal axis 99 of the elongate element 95 of gripping means 92 by a distance d3 which is equal to one-quarter of the transverse width, 753 (754) of the base of the pyramidal tooth-like element. The apex 715(b) (and hence apex 715(a) and 715(b)) of gripping means 90 is correspondingly displaced in equal distance d3' and the forward projection of the transverse terminal portion 703, 705 for a closed position in a smooth, essentially continuous circle as shown at 720 in the front elevation view of FIG. 7(A). The continuous periphery of the meshed terminal portions can be other than circular, e.g. rectangular 720' or elliptical 720" as shown in FIG. 7(c); however, a circular periphery is preferred as it provides maximum design strength consistent with passage through a round trocar tube. Similarly, while the preferred tooth-like element form is the pyrimidal form as described, other shapes can be used such as a wedge 722 as seen in FIG. 10(a) and a vertical faced pyramid 724 as shown in FIG. 10(b); both of which have a cross-section in the form of a triangle in a plane 726 passing therethrough and transverse to the longitudinal axis 97/99 thereof.

In the preferred embodiment shown in the drawings, the slope of the faces of the pyramidal elements is between 40° and 50° and the base 751 of the pyramidal elements, which define the forward terminal portions 703, 705 is about 1/10 to 1/20 of the length of elongate elements 93, 95. The height 753 of the pyramidal toothlike elements is from one to two times the width 755 of elongate elements 93, 95 with the foregoing structural arrangement, the end effector 40 of the present invention provides excellent tissue piercing and grasping capability while leaving a substantial space 760 between the gripping means 90, 92 which avoids pinching of adjacent tissue when the end effector 40 is in the closed position of FIG. 7.

A specific embodiment of the end effector of the present invention, as illustrated in FIG. 7, includes two gripping means having the following features:

| material | investment cast aluminum bronze |
| --- | --- |
| forward termination | two full and partial third quadrilateral pyramid in row of .198 inch slope 45°, height .088 inch, base .062 inch × .062 inch |
| elongate pivot arm (93, 95) | length = .83 inch, height = .055 inch, width = .095 inch |
| rearward portion 130, 132 | .140 inch pivot to pivot |

It will be appreciated that instead of the double-acting mechanism of FIG. 11, one of the gripping means e.g. 90' (shown in phantom) can be fixed positioned in-line with clevis 30 to provide a single action operation as hereinabove described.

Figure 11A:
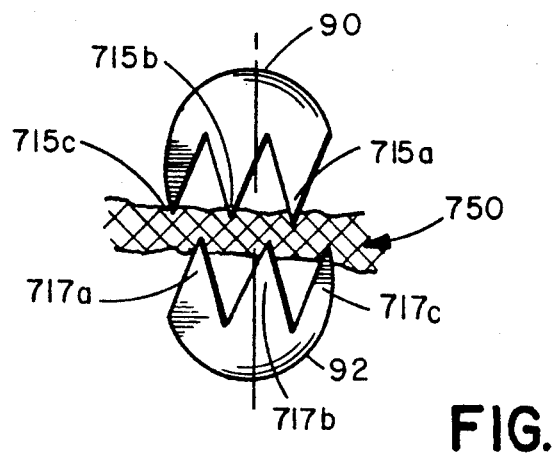
FIG. 11a is a front elevation view showing the device of FIG. 7 in an intermediate jaw position.
Figure 11:
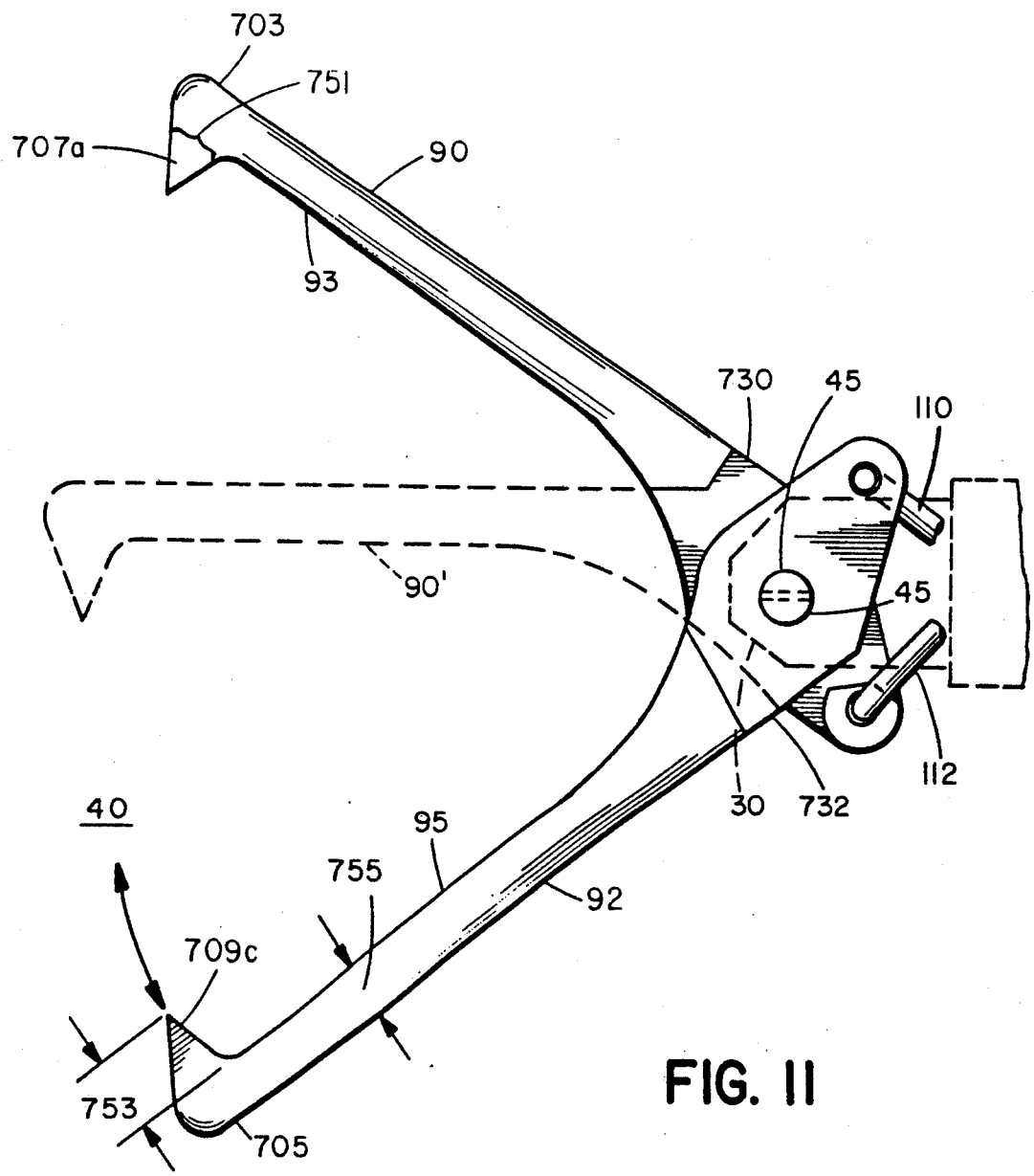
FIG. 11 is a side elevation view showing the device of FIG. 7 in an open jaw position, and in phantom showing the device in a closed jaw position.

In operation, the claw extractor end effector 40 of the present invention is assembled with the two essentially identical gripping means 90, 92 positioned to be facing oppositely and therefore in register (i.e., meshing) with each other with their respective tooth-like elements 707(a)-(c), 709(a)-(c) extending inwardly toward each other as shown in FIGS. 7 and 11. The gripping means 90, 92 are rotatably engaged at their rearward portions 730, 732 by a pivot screw 45 at a position spaced away from the respective forward terminal portions 703, 705. The gripping means 90, 92 are aligned so that their respective longitudinal axes 97, 99 are aligned so that their respective longitudinal axes 97, 99 lie in the plane of rotation 740 as indicated in FIGS. 7(b) and 7(c). The rearward portions of gripping means 90, 92 are pivotally engaged to linkage means 110, 112 to enable the gripping means to move, as hereinabove described, from the closed position of FIGS. 7, 7(a) where the tooth-like elements are meshed and are in close fitting contact, to the open position of FIG. 11, to the intermediate position of FIG. 11a where the respective toothlike elements are closing to pierce and grasp tissue 750.

With reference to FIGS. 12a and 12b, and in reference to another aspect of the invention, a ferrule type connecting means 910 is shown. Ferrule 910 provides a secure electrically insulating connection which peripherally bridges the exposed peripheral, electrically conductive, lateral portion 912 of aluminum tube 20 located between electrically insulating plastic shrink wrap 20 and the electrically insulating housing 914 of manually operable actuating means 50 which closely surrounds the aluminum tube 15. The portion of electrically insulating housing 914 adjacent the terminal portion 916 of electrically insulating shrink wrap 20 is provided with a flat-surfaced peripheral ridge 920. Ridge 920 has a substantially perpendicular wall 922 in the direction away from the shrink wrap 20. Wall 922 forms one side of a frusto-conical peripheral groove 921 which slopes upwardly away from perpendicular wall 922 until it terminates at wall 923. Ridge 920 further has a substantially frusto-conical surface 924 which slopes toward and is closely adjacent but slightly spaced from the shrink wrap 20 as indicated at 926.

Ferrule means 910 has a generally conical outer surface 929. The inner surface of ferrule means 910 is provided with a cylindrical passage 930 which is adapted to be closely adjacent to and surround a portion of shrink wrap 20, and is slidable with respect thereto. Contiguous to cylindrical passage 930, and coaxial therewith, is an outwardly flaring frusto-conical passage 932 which bridges and is spaced from the peripheral electrically conductive portion 912 of aluminum tube 20. Outwardly flaring frusto-conical passage 932 is bounded at its wider flared end by a flat peripheral rim of extension 934 which is adapted to abut the flat surfaced peripheral ridge 920 of the portion 914 of the electrically insulating housing 50. An axially inwardly depending perpendicular peripheral wall 936 of the outwardly flaring frusto-conical projection 938 abuts the peripheral wall 922 of the electrically insulating housing 914 of actuating means 50. Projection 938 is matingly seated in the extended frusto-conical peripheral groove 940 of the housing 914 and causes the ferrule connecting means 910 to be secured to the housing 914 while shielding the electrically conductive peripheral portion 912 of aluminum tube 20.

Ferrule connecting means 910 is suitably made of a strong, resilient, electrically insulating plastic material such as polypropylene or polycarbonate. In a preferred embodiment, the ferrule is a colored plastic, with the color utilized to identify the type of instrument of which it is a part. For example, a blue ferrule might identify a Maryland dissector, while a red ferrule might identify a single acting scissors. Regardless of color, the ferrule is installed by being moved slidably along shrink wrap 20 in the direction indicated at 945. When the ferrule means 910 is moved in the direction indicated, at some point, the portion of the frusto-conical projection 938 located adjacent wall 936 resiliently deforms outwardly to pass over rim 934 of rigid plastic housing 914. After wall 936 passes wall 922, the frusto-conical projection 938 snaps back into a mating engagement with groove 940 of the rigid plastic housing 914. In this mated position, the electrically insulating ferrule connecting means 910 overlaps peripheral electrical conductive portion 912 of aluminum tube 20 as well as substantial portions of the electrically insulating shrink wrap 20 and the electrically insulating housing 914. In this manner, the ferrule connecting means 910 reduces the possibility of electro-cautery burns to the practitioner.

The preferred endoscopy and laparoscopy instruments of the invention are preferably assembled in the following fashion. The knurled portion 34 of the clevis 30 of the invention is press fit inserted into the aluminum tube 15 which had been previously insert molded in the fixed handle portion 914, 410 of the actuating means 50. The aluminum tube 15 is crimped over the knurls 37 to effect mating. Shrink wrap 20 is then applied over the aluminum tube 15 and end-cut at grooves 380 in the arms 36 of the clevis 30. Ferrule 910 is slid over the distal end of the aluminum tube 15, up over the end of the housing 914, and snapped into place, thereby providing complete insulation. The rod 60, staples 110, 112, and end effectors (e.g. 90, 92) are assembled, with the staples coupling the rod to the end effectors. The rod is slid through the clevis and down the aluminum tube, until the end effectors are located between the arms of the clevis. When the holes in the proximal end of the end effectors (e.g. 96, 98) are lined up with the through-holes 39 in the arms of the clevis, the rotation post 45, which may either be integral with the clevis, or a separate post or nail, is inserted through the holes in the end effectors, and secured in the holes of the clevis arms such as by tapping. At this point, all that remains to be assembled is the actuating means 50. To assemble the actuating means, a cross pin 440 is inserted in handle 420. Handle 420 is then arranged such that the push rod 60 which extends out of the fixed handle portion will extend through the cross pin 440. With rod 60 in the cross pin 440, handle 420 is lined up with handle 410 such that the handle rotation pivot pin 430 can be inserted. With pivot pin 430 in place, and with the end effectors in the closed position, set screw 441 is tightened into the cross pin until it bites into rod 60, thereby holding rod 60 in place relative to cross pin 440.

There has been described and illustrated herein disposable surgical instruments. While particular embodiments of the invention have been described, it is not intended that the invention be limited exactly thereto, as it is intended that the invention be as broad in scope as the art will permit. Thus, while particular hermaphroditic end effectors were described, it will be appreciated that other end effectors other than claw extractors could be utilized, and that differently shaped claw extractors could be provided. For example, while the preferred embodiment show claw extractors where each gripping means has two full pyramidal teeth and one partial pyramidal tooth, it will be appreciated that the gripping means could have only two partial teeth, one full tooth and one partial tooth, one full tooth and two partial teeth, more than three teeth, etc. Also, while the claw extractors were described as having staple-like elements connecting the push rod to the end effectors and having end effectors which rotate about a single axis (the pin of the clevis) such as described in previously incorporated parent application Ser. No. 07/680,392, it will be appreciated that different arrangements such as provided in previously incorporated parent application Ser. No. 07/780,014 could be utilized to provide additional leverage to the end effectors. Also, while various materials were described as being preferred for various parts, it will be appreciated that other materials could be utilized. Therefore, it will be apparent to those skilled in the art that other changes and modifications may be made to the invention as described in the specification without departing from the spirit and scope of the invention as so claimed.

What is claimed is:

1. A surgical instrument for insertion through a trocar tube, comprising:
    a) a hollow tube having proximal and distal ends and a longitudinal axis;
    b) a push rod extending at least partly through said hollow tube;
    c) actuation means coupled to said push rod and coupled to said hollow tube for imparting reciprocal motion to said push rod relative to said hollow tube;
    d) end effector means comprising a first and second separately formed, identical, hermaphroditic, oppositely positioned gripping means having a base portion, an elongate element having a second longitudinal axis, and a distal portion, at least one of said first and second gripping means coupled at its base portion to said push rod, and said first and second gripping means coupled to said hollow tube, wherein said reciprocal motion of said push rod is translated into pivotal motion of said gripping means coupled to said push rod thereby causing said gripping means to be in either a closed meshed position or an open position, wherein
    said distal portion of said gripping means has a plurality of side by side tooth-like elements including at least one full tooth-like element and at least one partial tooth-like element, said tooth-like elements of each gripping means aligned along a third axis transverse said second longitudinal axis of said gripping means, and said tooth-like elements of each of said first and second gripping means extending in a direction transverse said second longitudinal axis and said third axis of said gripping means and towards the plurality of tooth-like elements of the other of said first and second gripping means, and wherein when said tooth-like elements are in said closed meshed position, said elongate elements are substantially parallel each other and displaced from each other along a fourth axis transverse said second longitudinal axes and said third axes, and a projection of said distal portion of said gripping means onto a plane perpendicular to said second longitudinal axes comprises a substantially solid circle.

2. A surgical instrument according to claim 1, wherein:
    all said tooth-like elements of said gripping means are asymmetrical relative to the respective second longitudinal axis of said gripping means.

3. A surgical instrument according to claim 2, wherein:
    said at least one full tooth-like element comprises two complete tooth-like elements.

4. A surgical instrument according to claim 3, wherein:
    said second longitudinal axes of said elongate elements are parallel to said longitudinal axis of said hollow tube when said tooth-like elements are in a closed meshed position.

5. A surgical instrument according to claim 3, wherein:
    each said full tooth-like element is a first quadrilateral based pyramid having a base with two sides parallel to said second longitudinal axes and two sides perpendicular to said second longitudinal axes, and each said partial tooth-like element comprises a part of a second quadrilateral base pyramid identical to a part of said first quadrilateral based pyramid.

6. A surgical instrument according to claim 2, wherein:
said side-by-side tooth-like elements comprise at least two substantially fully formed adjacent tooth-like elements and a partially formed tooth-like element in a row commencing with a substantially fully formed tooth-like element and terminating in a partially formed tooth-like element.

7. A surgical instrument according to claim 2, wherein:
each of said full tooth-like elements has a cross-section in a form of a triangle in a plane having first and second planar axes transverse to said second longitudinal axes, each said triangle having respective apexes, a distance being defined between apexes of adjacent said triangles, wherein a said apex of one of said triangles is transversely offset relative to said second longitudinal axis by one-quarter said apex-to-apex distance.

8. A surgical instrument according to claim 2, further comprising:
clevis means for coupling said end effectors to said hollow tube, said clevis means having a proximal portion fixedly coupled to said hollow tube and a distal portion having at least one pin transverse said longitudinal axis of said hollow tube, wherein
said respective base portions of said gripping means having respective first holes through which said at least one pin extends, at least one of said gripping means rotating around said at least one pin.

9. A surgical instrument according to claim 3, further comprising:
clevis means for coupling said end effectors to said hollow tube, said clevis means having a proximal portion fixedly coupled to said hollow tube and a distal portion having at least one pin transverse said longitudinal axis of said hollow tube, wherein
said respective base portions of said gripping means having first holes through which said at least one pin extends, at least one of said gripping means rotating around said at least one pin; and
coupling means for coupling said push rod to said gripping means, each gripping means having at least one second hole, said coupling means extending through said second hole of said rotating gripping means, and said coupling means connected to said push rod.

10. A surgical instrument according to claim 9, wherein:
said coupling means comprises two coupling elements, and each of said gripping means rotates around said at least one pin of said clevis means.

11. In a surgical instrument for insertion through a trocar tube, comprising a hollow tube having a first longitudinal axis, a push rod extending through said hollow tube, actuation means coupled to said push rod and to said hollow tube for moving said push rod relative to said hollow tube along said first longitudinal axis, and a pair of end effector means, at least one of said pair of end effector means coupled to said push rod and pivotally coupled to said hollow tube, wherein activation of said actuation means causes said end effector means to assume at least open and closed positions, an improvement comprising:
said pair of end effector means comprise a pair of identical oppositely positioned gripping means, each said gripping means having a base portion, an elongate element with a respective second longitudinal axis, and a forward terminal portion, each said terminal portion including a side-by-side row along a respective third axis perpendicular to said second axes of at least two tooth-like elements which are asymmetrical with respect to said second longitudinal axis of their respective elongate elements and which mesh in a close fitting contact when said actuation means cause said gripping means to assume said closed position, said row of tooth-like elements including at least one full tooth-like element and at least one partial tooth-like element, said tooth-like elements extending in a direction transverse said second longitudinal axis and said third axis of said gripping means and towards the plurality of tooth-like elements of the other of said first and second gripping means, and wherein when said tooth-like elements are in said closed position, said elongate elements are substantially parallel each other and displaced from each other along a fourth axis transverse said second longitudinal axes and said third axes, and a projection of said forward terminal portion of said gripping means onto a plane perpendicular to said second longitudinal axes comprises a substantially solid circle.

12. In a surgical instrument according to claim 11, wherein:
each full tooth-like element of a gripping means is in the form of an identical quadrilateral based pyramid having a base with two sides parallel to said second longitudinal axis of said gripping means and two sides perpendicular to said second longitudinal axis of said gripping means and
each partial tooth-like element is in the form of a part of said quadrilateral based pyramid.

13. In a surgical instrument according to claim 11, wherein:
said tooth-like elements each have a cross-section in the form of a triangle in a plane passing therethrough transverse to said longitudinal axis, each triangle having an apex, wherein the apex of one of said triangles is transversely displaced from said second longitudinal axis by one-quarter the distance between said apex and the apex of an adjacent triangular cross-section.

14. In a surgical instrument according to claim 13, wherein:
each apex of a tooth-like element of a particular gripping member is commonly offset from the second longitudinal axis of its respective elongate element.

15. In a surgical instrument according to claim 11, wherein:
said elongate elements are substantially greater in length than in width or height.

16. In a surgical instrument according to claim 12, wherein:
each said pyramid has four sloping sides, with the slope of each side of each pyramid being about between 40° and 50°.

17. In a surgical instrument according to claim 11, wherein:
said full tooth-like elements are in the form of identical wedges.

18. A surgical instrument according to claim 1, wherein:

each said full tooth-like element is a first quadrilateral based pyramid having a base with two sides parallel to said second longitudinal axes and two sides perpendicular to said second longitudinal axes, and each said partial tooth-like element comprises a part of a second quadrilateral base pyramid identical to a part of said first quadrilateral based pyramid.

19. A surgical instrument according to claim 18, wherein:

each said first quadrilateral based pyramid has four sloping sides, with the slope of each side of each pyramid being about between 40° and 50°.

20. A surgical instrument according to claim 5, wherein:

each said first quadrilateral based pyramid has four sloping sides, with the slope of each side of each pyramid being about between 40° and 50°.

* * * * *